United States Patent [19]

Carter et al.

[11] Patent Number: 5,432,193
[45] Date of Patent: Jul. 11, 1995

[54] ANTIBIOTIC LL-D37187α

[75] Inventors: Guy T. Carter, Suffern; Gerhard Schlingmann, Hillburn, both of N.Y.; David P. Labeda, Peoria, Ill.; Joseph J. Goodman, Spring Valley, N.Y.

[73] Assignee: American Cyanamid Company, Wayne, N.J.

[21] Appl. No.: 61,373

[22] Filed: May 14, 1993

[51] Int. Cl.6 .............................................. A61K 31/35
[52] U.S. Cl. ................................... 514/460; 549/343; 424/116
[58] Field of Search ..................... 549/343; 514/460; 424/116

[56] References Cited

U.S. PATENT DOCUMENTS

| | | | |
|---|---|---|---|
| 3,985,872 | 10/1976 | Chamberlin | 549/343 |
| 3,989,723 | 11/1976 | Hamill | 549/343 |
| 4,129,578 | 12/1978 | Celmar et al. | 549/343 |
| 4,293,650 | 10/1981 | Florent | 435/119 |
| 4,359,583 | 11/1982 | Mizutani et al. | 549/343 |
| 4,542,027 | 9/1985 | Clark | 549/343 |
| 4,804,680 | 2/1989 | Goudie et al. | 549/343 |
| 4,824,863 | 4/1989 | Hamill et al. | 514/460 |
| 5,043,353 | 8/1991 | Yao et al. | 514/460 |
| 5,064,855 | 11/1991 | Cullen et al. | 514/460 |
| 5,095,127 | 3/1992 | Goudie et al. | 549/343 |

*Primary Examiner*—C. Warren Ivy
*Assistant Examiner*—A. A. Owens
*Attorney, Agent, or Firm*—T. S. Szatkowski

[57] ABSTRACT

This invention relates to antibiotic LL-D37187α derived from the microorganism Streptomyces which is useful as an antibacterial agent.

4 Claims, 3 Drawing Sheets

ANTIBIOTIC LL-D37187α

BACKGROUND OF THE INVENTION

1. Field of the Invention

The invention relates to a new antibiotic designated LL-D37187α, to its production by fermentation, to methods for its recovery and concentration from crude solutions and to processes for its purification. The present invention includes within its scope the agent in dilute form, as a crude concentrate, in pure form and a novel strain of Streptomyces. The present invention also relates to the use of the compound according to the invention in antimicrobial compositions such as antiseptics, disinfectants or preservatives.

2. Description of the Prior Art

Other related antibiotics are described in the literature. Tsuji, N., K. Nagashima, Y. Terui and K. Tori, report the structure of K-41B, a new diglycoside polyether antibiotic in The Journal of Antibiotics, 32, 169–172 (1979); Dirlam, J. P., Bordner, J., W. P. Cullen, M. J. Jefferson and L. Presseau-Linabury report the structure of CP-96,797, a polyether antibiotic related to K-41A and produced by Streptomyces sp in The Journal of Antibiotics, 45, 1187–1189 (1992); and in U.S. Pat. No. 4,293,650 the anticoccidial substance 37,454 RP is reported by Florent, J., Lunel, J. and Marcy, D.

DESCRIPTION OF THE PREFERRED EMBODIMENTS

The structure of the new antibiotic LL-D37187α is:

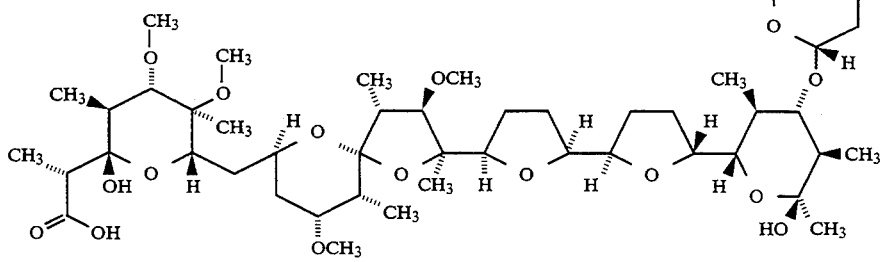

Figure 1:
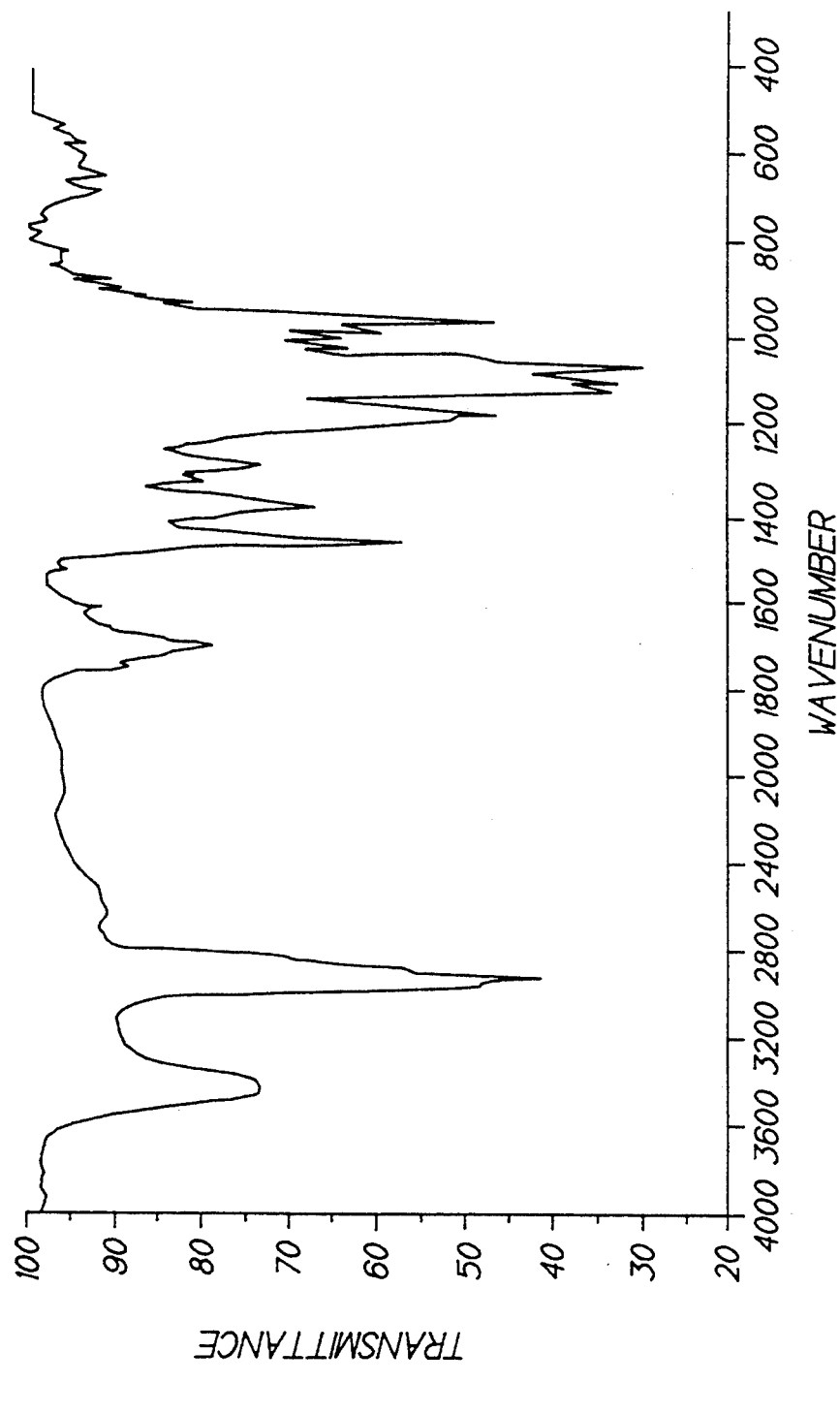
FIG. 1 shows an infrared absorption spectrum of LL-D37187α.
Figure 2:
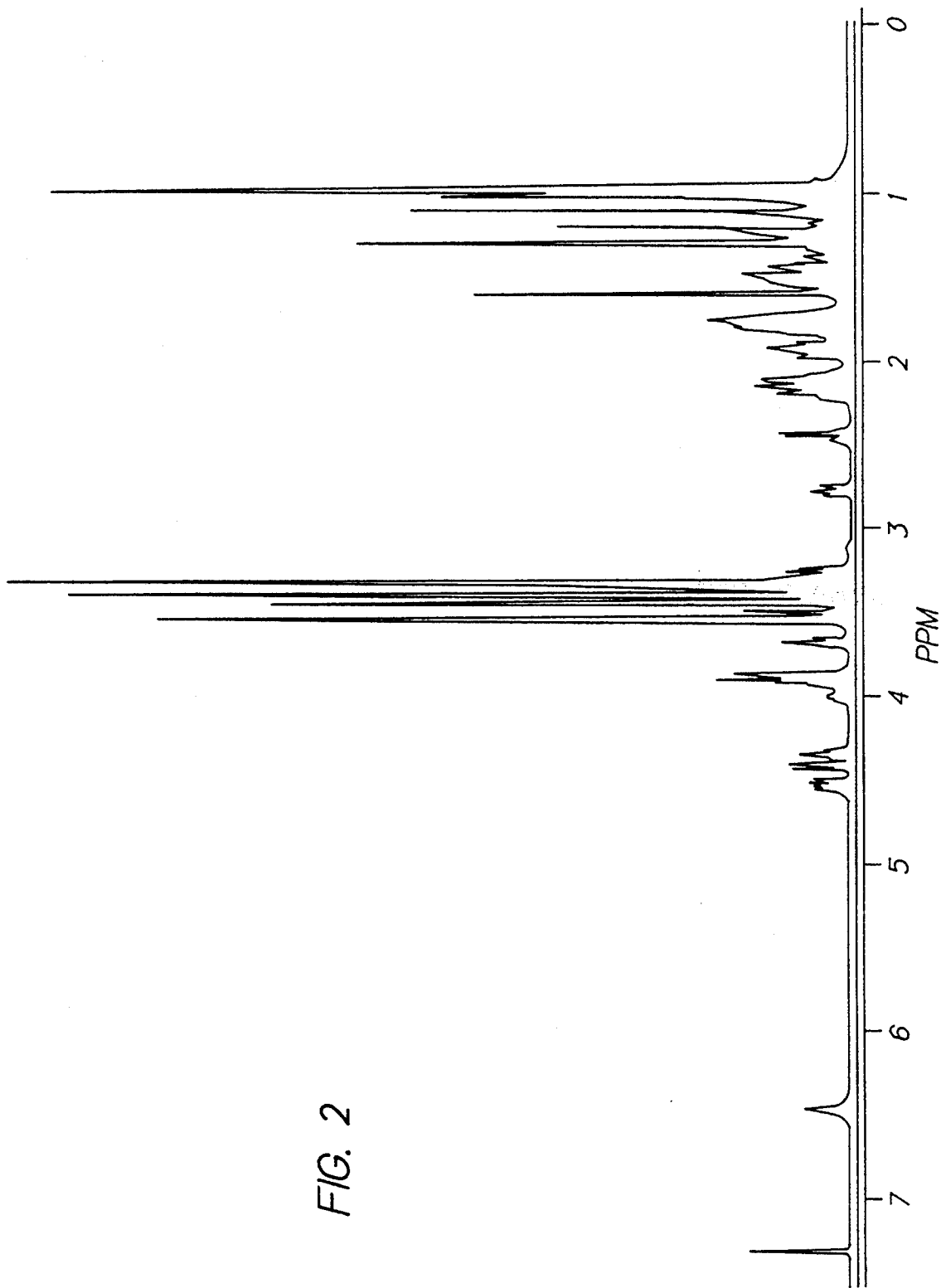
FIG. 2 shows a proton magnetic resonance spectrum of LL-D37187α.
Figure 3:
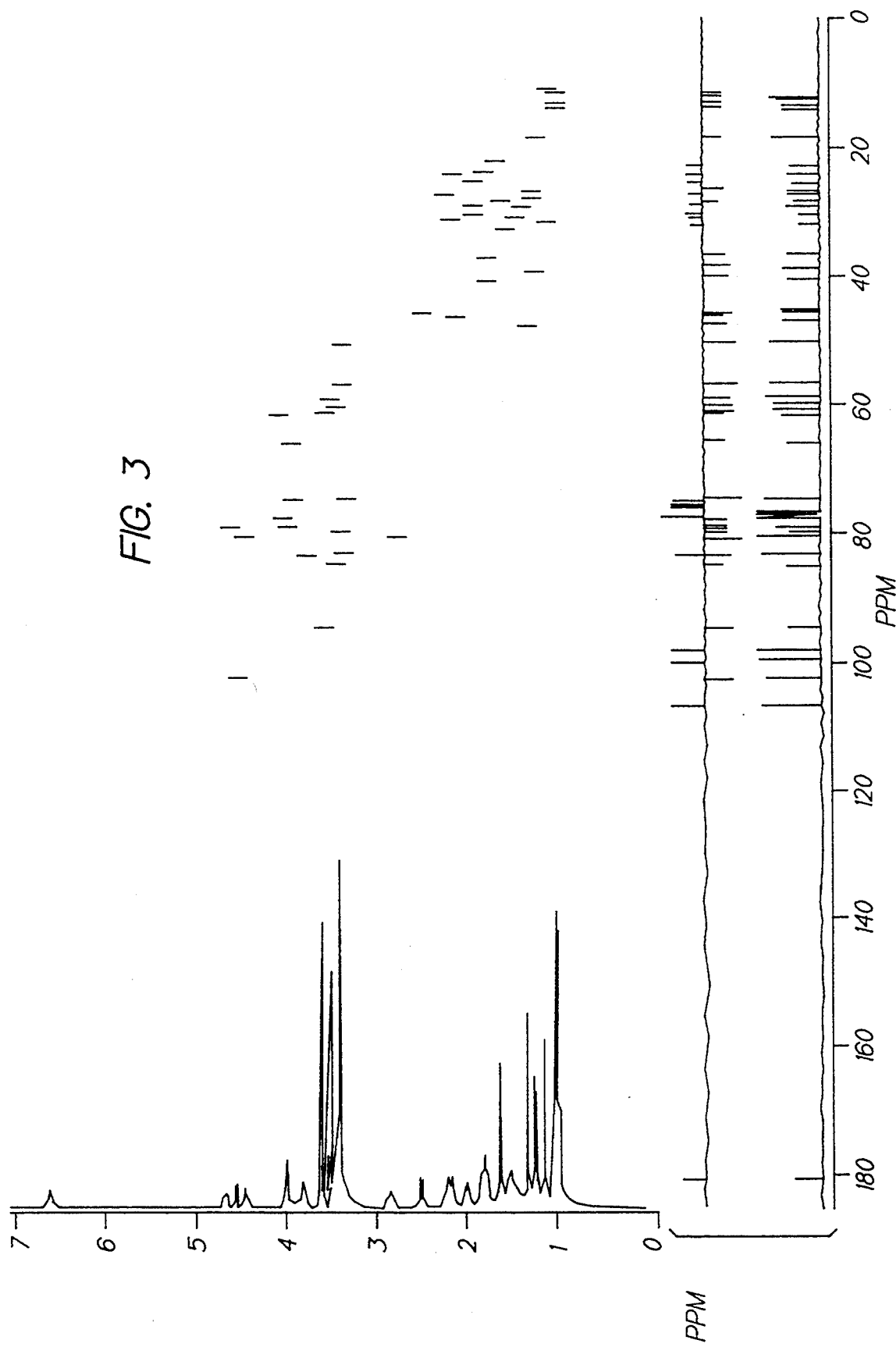
FIG. 3 shows a carbon-13 nuclear magnetic resonance spectrum of LL-D37187α.

The physico-chemical characteristics of LL-D37187α are as follows:

1. Molecular weight: 944(FABMS);
2. Apparent molecular formula: $C_{49}H_{84}O_{17}$;
3. A specific optical rotation; $[\alpha]_D^{26} = +21°$ (C 1.018%, $CHCl_3$);
4. Infrared absorption spectrum as shown in FIG. 1 (KBrdisc) significant peaks as listed below: 3443, 2971, 2934, 2830, 1700, 1459, 1377, 1287, 1165, 1119, 1101, 1069, 1020, 1002, 983, 957 $cm^{-1}$;
5. Proton nuclear magnetic resonance spectrum: as shown in FIG. 2 (300 MHz, $CDCl_3$);
6. Carbon-13-nuclear magnetic resonance spectrum: as shown in FIG. 3 (75 MHz, $CDCl_3$, ppm downfield from TMS) significant peaks as listed below:

| | | |
|---|---|---|
| 180.76 | 74.37 | 30.47 |
| 106.74 | 65.75 | 29.13 |
| 102.62 | 61.32 | 28.38 |
| 99.60 | 60.89 | 27.30 |
| 98.28 | 60.14 | 26.60 |
| 94.70 | 59.02 | 25.57 |
| 84.63 | 56.74 | 24.12 |
| 83.38 | 50.49 | 22.95 |
| 83.24 | 47.07 | 18.25 |
| 83.16 | 46.03 | 13.32 |
| 80.37 | 45.58 | 12.73 |
| 80.34 | 40.47 | 12.58 |
| 79.63 | 38.98 | 11.88 |
| 79.23 | 36.88 | 11.46 |
| 79.07 | 32.56 | 11.46 |
| 78.37 | 31.24 | 11.36 |
| 74.39 | | |

The new antibacterial agent LL-D37187α is formed during the cultivation under controlled conditions of a new strain of Streptomyces.

This microorganism is maintained in the culture collection of the Medical Research Division, American Cyanamid Company, Pearl River, N.Y. 10965 as culture LL-D37187α. A viable culture of this new microorganism has been deposited under conditions of the Budapest Treaty with the Patent Culture Collection Laboratory, Northern Regional Research Center, U.S. Department of Agriculture, Peoria, Ill. 61604, and has been added to its permanent collection. It has been assigned the strain designation NRRL 21087 by said depository.

Culture LL-D37187 is isolated from a soil sample taken from Pomeroy, Wash., under a sage brush.

Culture LL-D37187 has the following cultural characteristics as described in Table I.

TABLE I

CULTURAL CHARACTERISTICS

| Characteristic | D37187 |
|---|---|
| Aerial Mycelium | Spirals |
| Fragmentation of Substrate Mycelium | None |
| Zoospores and Sporangia | None |
| Spore Chain | 15–20 |
| Spore Shape | Cylindrical |
| Spore Surface | Smooth |
| Temperature Growth | 22–45° C. |
| Salt Tolerance | >5% |
| DAP Analysis | LL-DAP |
| Whole cell Sugars | Ribose, Mannose, Inositol, Galactose |

The macromorphology for culture LL-D37187 is described in Table II.

TABLE II

MACROMORPHOLOGY

| Medium | D37187 Morphology[a] |
|---|---|
| Yeast-Malt (ISP2) | G: Abundant<br>AM: White (263)<br>SM: Pink-Yellow to Medium Yellow (89,87)<br>SP: None |
| Oatmeal (ISP3) | G: Abundant<br>AM: White (263)<br>SM: Pink-Yellow (89)<br>SP: None |
| Inorganic Salts-Starch (ISP4) | G: Sparse<br>AM: Yellow-White (92)<br>SM: Yellow-White (92)<br>SP: None |
| Glycerol-Asparagine (ISP5) | G: No Growth<br>AM: None<br>SM: None<br>SP: None |

G, growth; AM, aerial mycelium; SM, substrate mycelium; SP, soluble pigment
[a]ISCC, National Bureau of Standard Centroid Color Charts, Publication 440, Washington, D.C., 1976.

The physiological reactions of LL-D37187 are shown in Table III.

TABLE III

PHYSIOLOGICAL REACTIONS OF LL-D37187

| | |
|---|---|
| Utilization of carbon Sources: | |
| D-Glucose | + |
| L-Arabinose | + |
| Sucrose | − |
| D-Xylose | ± |
| I-Inositol | ± |
| D-Mannitol | − |
| β-D-Fructose | + |
| a-L-Rhamnose | + |
| Raffinose | − |
| Cellulose | − |
| Hydrolysis of: | |
| Casein | + |
| Xanthine | − |
| Hypoxanthine | + |
| Tyrosine | ± |
| Adenine | − |
| Esculin | + |
| Production of: | |
| Urease | + |
| Melanin | − |
| Decarboxylation of: | |
| Acetate | − |
| Benzoate | − |
| Citrate | + |
| Lactate | + |
| Malate | + |
| Mucate | − |
| Oxalate | − |
| Proprionate | − |
| Pyruvate | + |
| Succinate | + |
| Tartrate | ± |
| Acid Production from: | |
| Arabinose | + |
| Dulcitol | − |
| Erythritol | − |
| Glucose | + |
| Inositol | − |
| Lactose | − |
| Mannitol | − |
| Mannose | + |
| Methyl-a-D-glucoside | − |
| Melibiose | − |
| Raffinose | − |
| a-L-Rhamnose | + |
| Sorbitol | − |

TABLE III-continued

PHYSIOLOGICAL REACTIONS OF LL-D37187

| | |
|---|---|
| Trehalose | + |

+: positive, −: negative, ±: weak

It is to be understood that for production of these new antibacterial agents the present invention is not limited to this particular organism or to organisms fully answering the above characteristics which are given for illustrative purposes only. In fact, it is desired and intended to include the use of mutants produced from this organism by various means such as exposure to X-radiation, ultraviolet radiation, N'-methyl-N'-nitro-N-nitrosoguanidine, actinophages and the like.

The in vitro antibacterial activity of LL-D37187α is determined against a spectrum of gram-positive and gram-negative bacteria by a standard agar dilution method Mueller-Hinton agar with 5% sheep blood and two-fold decreasing concentrations of LL-D37187α is poured into petri dishes. The agar surfaces are inoculated with 1 to $5 \times 10^4$ colony forming units of bacteria by means of the Steers replicating device. The lowest concentration of antibiotic that inhibits growth of a bacterial strain after 18 hours incubation is recorded as the minimal inhibitory concentration for that strain. The antibacterial results are given in Table IV with sheeps blood added to the agar.

TABLE IV

In vitro Antibacterial Activity of LL-D37187α
In the Presence of Sheeps Blood

| Organism | Minimum Inhibitory Concentration mcg/ml LL-D37187α |
|---|---|
| 1. Staphylococcus aureus (87-69) | 2 |
| 2. Staphylococcus aureus Rose MP | 1 |
| 3. Staphylococcus aureus IVES (542) | 1 |
| 4. Staphylococcus aureus NEMC (89-3) | 1 |
| 5. Staphylococcus aureus IVES (396) | 2 |
| 6. Staphylococcus haemolyticus AVAH (88-1) | 2 |
| 7. Staphylococcus haemolyticus (88-3) | 1 |
| 8. Coagulas negative staphylococcus (1109) | 2 |
| 9. Coagulas negative staphylococcus (1181) | 1 |
| 10. Bacillus cereus Davies | 0.5 |
| 11. E. faecium ARUM (87-41) | 0.5 |
| 12. E. faecium Gp.D. WRVA (88-33) | 1 |
| 13. E. faecium (12201) | 1 |
| 14. E. faecium (12202) | 0.5 |
| 15. E. faecium VCI (85-30) | 0.12 |
| 16. E. faecium NEMC (89-2) | 2 |
| 17. Enterococcus faecalis AMCH (88-84) | 0.5 |
| 18. Enterococcus faecalis AMCH (88-86) | 0.5 |
| 19. Streptococcus pneumoniae CHBM (88-70) | ≦0.06 |
| 20. Streptococcus pneumoniae CHBM (88-75) | ≦0.06 |
| 21. Streptococcus pneumoniae TEX (85-2) | ≦0.06 |
| 22. Staphylococcus aureus 29213 | 2 |
| 23. Staphylococcus aureus NEMC (89-5) | 4 |
| 24. E. coli D21 | >128 |
| 25. E. coli D22 | >128 |
| 26. E. coli ATCC (25922) | >128 |
| 27. E. coli ATCC (35218) | >128 |
| 28. Staphylococcus aureus ATCC (25923) | 2 |
| 29. Staphylococcus aureus VGH (84-47) | 1 |
| 30. Staphylococcus aureus K (82-26) | 2 |

TABLE IV-continued

In vitro Antibacterial Activity of
LL-D37187α
In the Presence of Sheeps Blood

| Organism | Minimum Inhibitory Concentration mcg/ml LL-D37187α |
|---|---|
| 31. *Staphylococcus aureus* CMC (83-131) | 2 |

The antibacterial results show that the product according to the invention has a broad spectrum of activity against the bacterial strains tested.

The product according to the invention, which has good antimicrobial activity can be used in antimicrobial compositions, especially as an antiseptic by local and general application, and as a disinfectant.

As antiseptics for human or veterinary use, the concentration of active product can vary from 0.01% to 5% by weight according to the use and the chosen formulation. Thus, it is possible to prepare foaming detergent solutions to be used by surgeons and nursing staff for washing their hands or to be used for cleansing dermatological lesions such as impetigo, pityriasis and leg ulcers. Foaming detergent solutions are also used as shampoos (for example antidandruff shampoos) or for the preparation of shower gels, shaving creams and foaming lotions. Foaming solutions containing product according to the invention are obtained using amphoteric, anionic, cationic or non-ionic surfactants at a concentration of 0.3 to 30%, humectants such as glycols or polyethylene glycols, at a concentration of 0 to 20% ethylene oxide and polypropylene copolymers at a concentration of 0 to 20%, and an alcohol (ethanol, isopropanol, benzyl alcohol) or a polyol, such as glycerol, at a concentration of 0 to 15%, as well as agents for complexing $Ca^{++}$, $Mg^{++}$ and heavy metal ions, salts for providing an appropriate buffer capacity, agents for imparting viscosity, such as NaCl or KCl, natural, cellulosic or synthetic polymers such as polyvinylpyrrolidone, thickening superfatting agents such as polyethylene glycol distearate or copra monoethanolamide or diethanolamide, fragrances, preservatives and colorants.

If the product according to the invention has a poor solubility in water, it is possible to use microemulsions, micellar solutions or any other phase of the ternary or quaternary diagram of water/active principle/surfactant/co-surfactant which permits solubilization in water. These solutions can be used in diluted or undiluted form and can be dispensed for example by means of a vasopump or liquefied or non-liquefied propellants.

With the same constituents at appropriate concentrations, the product according to the invention can also be used to prepare simple aqueous solutions or aqueous solutions in the form of sprays for making operative fields antiseptic, for postoperative treatments, for the treatment of burns, superinfected eczema, gluteal erythema, wounds or acne, or for deodorants.

Simple alcoholic solutions or alcoholic solutions in the form of sprays containing 20 to 80% by weight of alcohol can contain, apart from the excipients used in aqueous solutions, excipients which make it possible to penetrate the keratinized layers of the skin and superficial body growths, such as Azone (marketed by Nelson Research) and Transcutol (marketed by Gattefosse). These solutions are to be used for making the skin antiseptic before puncture, for preparing the operative field, by nursing staff for making their hands antiseptic and for treating closed infected dermatosis, folliculitis, perionychia or acne.

The product according to the invention can be applied in the form of creams which contain compound mentioned for the preparation of solutions, together with the fatty substances normally found in the preparation of creams or emulsions. These creams can be used especially for the prevention of superinfections of gluteal erythema, eczema, mycosis or acne.

The product according to the invention can also be used in animals for indications such as the prevention or treatment of infected lesions or lesions liable to become superinfected. In this case, the pharmaceutical compositions are similar to those used in man, in particular creams sprays or solutions.

Moreover, the rapid lethal action on germs of the products according to the invention enables them to be used as surface disinfectants at concentrations which can vary from 0.1 to 4% by weight. In this case, the product is used in preparations such as aqueous or non-aqueous foaming detergent solutions, sprays or nebulizers. Preparations of this type are particularly useful in the hospital or veterinary sectors, for local communities or agrifoodstuff industries. These preparations can contain the same constituents as those used in the antiseptic formulations, although a variety of organic solvents may be added.

Finally, the antimicrobial activity of these products enables them to be used as preservatives in the pharmaceutical, cosmetic and food industries. In this case, the product according to the invention is used as an additive for pharmaceutical, cosmetic or food formulations at concentrations which can vary from 0.005 to 0.5%. The compounds can also be used as disinfectant additives in paints.

In therapeutic use, the compound of this invention may be administered in the form of conventional antimicrobial pharmaceutical compositions appropriate for the intended use.

GENERAL FERMENTATION CONDITIONS

Cultivation of Streptomyces LL-D37187 may be carried out in a wide variety of liquid culture media. Media which are useful for the production of LL-D37187α include an assimilable source of carbon, such as dextrin, sucrose, molasses, glycerol, etc.; an assimilable source of nitrogen, such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicon oil may be added as needed.

GENERAL PROCEDURE FOR THE ISOLATION OF LL-D37187α

The LL-D37187α is recovered from the fermentation broth by extracting with ethyl acetate and partitioning the extract between aqueous methanol and hexane. The hexane is evaporated and the concentrate purified by chromatography on silica gel by elution with 1:3 ethyl acetate-hexane to give LL-D37187α as the sodium salt.

The invention will be further described in conjunction with the following non-limiting examples.

EXAMPLE 1

Inoculum Preparation

A typical medium used to grow the primary inoculum is prepared according to the following formula:

| | |
|---|---|
| Glucose | 1.0% |
| Dextrin | 2.0% |
| Yeast extract | 0.5% |
| NZ Amino A ®[1] | 0.5% |
| Calcium carbonate | 0.1% |
| FD-82 defoamer | 0.3% |
| Water qs | 100.0% |

1 [NZ Amine A[1] is a pancreatic digest of casein, registered trademark of Sheffield chemical, Norwich, NY]

This medium is sterilized and 100 ml, in a 500 ml flask, is inoculated with Streptomyces. The medium is then placed on a rotary shaker operating at 200 rpm and incubated at 32° C. for 24 hours providing a primary inoculum. This primary inoculum is then used to inoculate 10 liters of the same sterile medium in a 14 liter tank. This medium is grown at 32° C. for 24 hours with a sterile air flow of 10 liters per liter of mash per minute and agitation by an impeller driven at 450 rpm, providing a tertiary inoculum.

EXAMPLE 2

Fermentation

A fermentation medium of the following formulation is prepared:

| | |
|---|---|
| Molasses | 2.0% |
| Dextrin | 1.0% |
| Soy flour | 1.5% |
| Calcium carbonate | 1.0% |
| FD-82 defoamer | 3.0% |
| Water qs | 100.0% |

This medium is sterilized and 300 liters is then inoculated with the tertiary inoculum of Example 1. The fermentation is conducted at 28° C. with a sterile air flow of 250 liters per minute and agitation by an impeller driven at 250 rpm for 96 hours, at which time the mash is harvested.

EXAMPLE 3

Isolation and Purification of LL-D37187α

The mash is mixed with 1% by volume of toluene, 200 liters of ethyl acetate and stirred for 4 hours. The organic layer is separated and evaporated to an oily residue.

Isolation of LL-D37187α

The oily residue obtained upon evaporation of the ethyl acetate extract of the whole fermentation mash is partitioned between hexane and wet methanol (5% $H_2O$). The hexane layer containing the bulk of the polyether is evaporated to an oil. Trituration of this oil with methanol (2×250 mL) provides a solution of material suitable for chromatography. The residue obtained upon concentration of the methanol is redissolved in ethyl acetate:hexane (1:3), and is charged onto a silica gel (100 g, 63–200 micron) column (2.5×35 cm) packed in the same solvent mixture. The column is developed with this solvent mixture at flow rate of 4.0 mL per minute and fractions are collected at 6.5 minute intervals. Fractions are assayed by TLC on silica gel (silica gel GF, ethyl acetate mobile phase, detected with vanillin-$H_2SO_4$ spray). Combining fractions 21–30 yields upon concentration a colorless film, which is dissolved in t-butanol and freeze dried to give LL-D37187α (180 mg) as a fluffy white solid: $C_{49}H_{84}O_{17}$, mol. wt. 944; $[\alpha]_D^{26} = +21°$ (c 1.018%, $CHCl_3$); IR (KBr) 3443, 2971, 2934, 2830, 1700, 1459, 1377, 1287, 1165, 1119, 1101, 1069, 1020, 1002, 983, 957 cm$^{-1}$; $^1$H & $^{13}$C NMR see FIG. 3 and FIG. 4; FABMS [M+Na]$^+$=M/Z 967; HRFAB-MS, calcd. for $C_{49}H_{84}O_{17}$·Na=M/Z 967.5606; obs. M/Z 967.5675. Soluble in organic solvent, insoluble in water.

What is claimed is:

1. The compound LL-D37187α which has the structure:

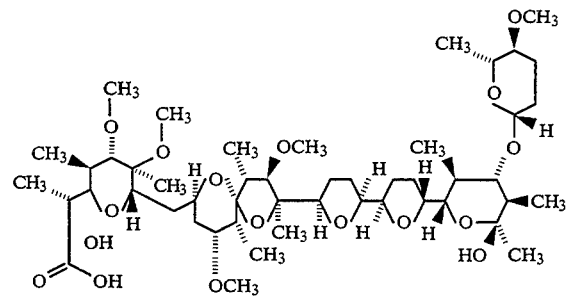

and the following physico-chemical characteristics:
1. Molecular weight: 944 (FABMS);
2. Apparent molecular formula: $C_{49}H_{84}O_{17}$;
3. A specific optical rotation: $[\alpha]_D^{26} = +21°$ (C 0.018% $CHCl_3$);
4. Infrared absorption spectrum as shown in FIG. 1 (KBrdisc) with significant peaks as follows: 3443, 2971, 2934, 2830, 1700, 1459, 1377, 1287, 1165, 1119, 1101, 1069, 1020, 1002, 983, 957 cm$^{-1}$;
5. Proton nuclear magnetic resonance spectrum: as shown in FIG. 2 (300 MHz, $CDCl_3$):
6. Carbon-13-nuclear magnetic resonance spectrum: as shown in FIG. 3 (75 MHz, $CDCl_3$, ppm downfield from TMS) significant peaks as listed below:

| | | |
|---|---|---|
| 180.76 | 74.37 | 30.47 |
| 106.74 | 65.75 | 29.13 |
| 102.62 | 61.32 | 28.38 |
| 99.60 | 60.89 | 27.30 |
| 98.28 | 60.14 | 26.60 |
| 94.70 | 59.02 | 25.57 |
| 84.63 | 56.74 | 24.12 |
| 83.38 | 50.49 | 22.95 |
| 83.24 | 47.07 | 18.25 |
| 80.37 | 46.03 | 13.32 |
| 80.34 | 45.58 | 12.73 |
| 79.63 | 40.47 | 12.58 |
| 79.23 | 38.98 | 11.88 |
| 79.07 | 36.88 | 11.46 |
| 78.37 | 32.56 | 11.46 |
| 74.39 | 31.24 | 11.36 |

2. A pharmaceutical, disinfectant or cosmetic composition which contains an effective antimicrobial, disinfectant or preservative amount of LL-D37187α of claim 1 as an active ingredient.

3. A pharmaceutical composition having antimicrobial and disinfectant activity as claimed in claim 2, wherein said effective amount of said antimicrobial compound LL-D37187α is from 0.01 to 5% by weight.

4. A disinfectant composition for inert surfaces as claimed in claim 2 wherein said effective amount of said antimicrobial compound LL-D37187α is from 0.1 to 4% by weight.

* * * * *

UNITED STATES PATENT AND TRADEMARK OFFICE
CERTIFICATE OF CORRECTION

PATENT NO. : 5,432,193
DATED : Jul. 11, 1995
INVENTOR(S) : Guy T. Carter, et al

It is certified that error appears in the above-indentified patent and that said Letters Patent is hereby corrected as shown below:

In claim 1, at column 8, lines 15-26 delete the structure:

"
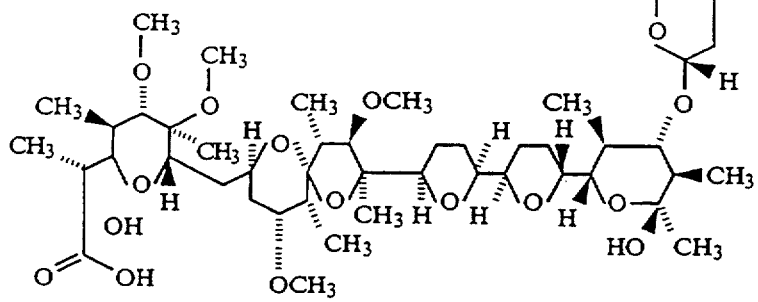
"

and insert the structure:

--
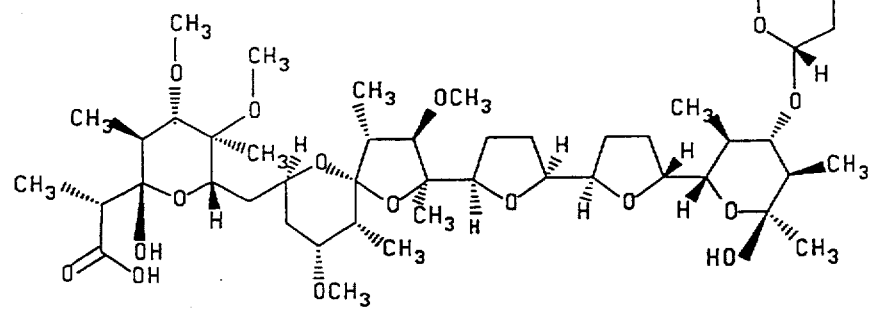
--

UNITED STATES PATENT AND TRADEMARK OFFICE
CERTIFICATE OF CORRECTION

PATENT NO. : 5,432,193  
DATED : Jul, 11, 1995  
INVENTOR(S) : Guy T. Carter, et al It is certified that error appears in the above-indentified patent and that said Letters Patent is hereby corrected as shown below:

Column 8, at line 32, delete "0.018% $CHCl_3$);" and insert --1.018%, $CHCl_3$);--therefor.

Signed and Sealed this

Nineteenth Day of September, 1995

Attest:

BRUCE LEHMAN

Attesting Officer

Commissioner of Patents and Trademarks